United States Patent [19]

Francese et al.

[11] Patent Number: 4,502,881

[45] Date of Patent: Mar. 5, 1985

[54] WEED-KILLING FURAZAN COMPOUNDS

[75] Inventors: Renato Francese, Moncalieri; Roberta Fruttero, Sabiliano; Vittorio Messori; Anna Peluffo, both of Turin, all of Italy

[73] Assignee: ANIC S.p.A., Palermo, Italy

[21] Appl. No.: 593,772

[22] Filed: Mar. 27, 1984

[30] Foreign Application Priority Data

Mar. 29, 1983 [IT] Italy ................ 20341 A/83

[51] Int. Cl.$^3$ .......................................... A01N 43/82
[52] U.S. Cl. ................................................ 71/92
[58] Field of Search ........................................ 71/92

[56] References Cited

U.S. PATENT DOCUMENTS

| | | | |
|---|---|---|---|
| 3,410,676 | 11/1968 | Hill | 71/77 |
| 3,917,478 | 11/1975 | Moser et al. | 71/90 |
| 3,937,715 | 2/1976 | Rochling et al. | 71/92 X |
| 4,243,409 | 1/1981 | Schmidt et al. | 71/92 |
| 4,259,104 | 3/1981 | Edwards | 71/92 |

*Primary Examiner*—Catherine L. Mills
*Attorney, Agent, or Firm*—Sughrue, Mion, Zinn, Macpeak and Seas

[57] ABSTRACT

The description relates to heterocyclic compounds having weed-killing activity and defined by the following general formula:

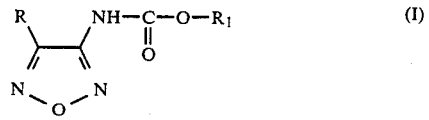

where R is a straight-chain or branched alkyl group with 1 to 6 carbon atoms or the phenyl group, $R_1$ is a straight-chain or branched alkyl group with 1 to 10 carbon atoms (substituted if required by halide, or phenyl group), an alkenyl group, an alkynyl group, a cycloalkyl group, or the phenyl group.

3 Claims, No Drawings

WEED-KILLING FURAZAN COMPOUNDS

The invention relates ro heterocyclic weed-killing compounds and their use for destroying weeds.

As is known, in agriculture there is a great need for novel alternative herbicidal products having high activity in eliminating weeds combined with substantial harmlessness towards man and animals.

According to the invention, these requirements are satisfied by novel herbicidal compounds having a heterocyclic structure.

To this end, the invention relates to a method of controlling the growth of weeds, characterised in that the infested land is treated with an effective quantity of at least one herbicidal coumpound chosen from those defined by the following general formula:

$$\underset{N\diagdown_O\diagup N}{\overset{R}{\underset{H}{\diagdown}}\!\!\!\diagup\!\!\!\overset{N-C-O-R_1}{\underset{\|}{\|}}}\quad (I)$$

where

R is a straight-chain or branched alkyl group with 1 to 6 carbon atoms or the phenyl group, $R_1$ is a straight-chain or branched alkyl group with 1 to 10 carbon atoms substituted if required by halide or phenyl group, an alkenyl group, an alkynyl group, a cycloalkyl group, or the phenyl group.

Some of the compounds represented by the general formula (I) are known in the literature, which describes their synthesis, physical and chemical characteristics, and, in some cases, their pharmacological properties. The known compounds have been synthesized by the Istituto di Chimica Farmaceutica at Turin University (Italy).

The following literature should be consulted:
Chemical Abstract Registry Number 32551-36-3; 32551-38-5; 17647-70-0; 32551-40-9;
A. Gasco et al. Farmaco Ed. Sci., 26, 241 (1971),
A. Gasco et al., Farmaco Ed. Sci., 32, 789 (1977)
A. Fundaro, Bull. Soc. Ital. Biol. Sper., 50, 1650 (1974);
A. Gasco et al. J. Heterocycl. Chem., 9, 837 (1972)
Swiss PS No. 502 365;
GB PS No. 1 124 920

The invention is based on the discovery that the aforementioned known compounds and other novel compounds represented by the aforementioned general formula (I) have herbicidal activity with a wide range of action against weeds but are substantially harmless towards man and animals.

Compounds (I) can be synthesized by using the following reaction scheme:

$$R-CO-CN_2-COOEt \xrightarrow{NaNo_2} R-CO-CH=NOH \quad (a)$$

$$R-CO-CH-NOH \xrightarrow{2NH_2OH} \underset{N\diagdown_O\diagup N}{\overset{R}{\diagdown}\!\!\!\diagup\!\!\!\overset{NH_2}{}} \quad (b)$$

$$\underset{N\diagdown_O\diagup N}{\overset{R}{\diagdown}\!\!\!\diagup\!\!\!\overset{NH_2}{}} \xrightarrow{D\ COOR_1} \underset{N\diagdown_O\diagup N}{\overset{R}{\diagdown}\!\!\!\diagup\!\!\!\overset{NH-COOR_1}{}} \quad (I) \quad (c)$$

In the preceding formulae R and $R_1$ have the meanings previously given and X denotes a halogen, usually chlorine, atom.

With regard to the synthesis of compounds (I), the following literature should also be referred to:
Berichte, 13, 1328, (1882);
Gazz. Chim. Ital. 81, 106, (1951).

Compounds (I) according to the invention have high herbicidal activity when used either before or after the emergence or crops in doses of from 0.1 kg/ha up to a maximum of 5 kg/ha.

In addition, the herbicidal activity of compounds (I) is highly selective towards crops belonging to the graminaceae families, e.g. species of wheat and maize, up to doses of 3 kg/ha; at higher doses the herbicidal activity of the compounds become total.

Compounds (I) according to the invention are herbicides with interfere with the seed germination phase and in the subsequent growth of the embryo plant. They have good herbicidal activity and can conveniently be used for weed-killing, particularly after a crop has appeared, in dependence on the varying degrees of selectivity shown by them and the biological cycle of the weeds.

Compounds (I) according to the invention can be used as such but in the preferred embodiment of the invention they are formulated in solution, suspension, emulsion, powder or granulates depending on the chosen application, provided the active principle is finely divided.

Typically, the compositions of the present invention are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficiency. By the term "surface-active agents" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, polyoxyethylene derivatives of alkylphenols (particularly isooctylphenol and nonylphenol).

Water-dispersible powder compositions can be made containing one or more active ingredients, an inert solid extender and one or more wetting and dispersing agents. The inert solid extenders are usually of mineral origin such as the natural clays, diatomaceous earth and synthetic mineral derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition.

Aqueous suspensions can be prepared by mixing together and grinding an aqueous slurry of water-insoluble active ingredient in the presence of dispersing agents to obtain a concentrate slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface-active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface-active agent and about 4 to 94 parts solvent, all parts being by weight based on the total weight of emulsifiable oil.

The following experimental examples are given for non-limitatively illustrating the invention.

EXAMPLE 1

Preparation of cyclohexyl ester of 4-methyl-3-furazan carbamic acid

First, 3-amine-4-methyl-furazan was prepared via isonitroso-acetone by the general method disclosed in Berichte 13, 1328 (1882) followed by cyclization as described in Gazz. Chim. Ital. 81, 106, (1951).

Next, 30 g (about 0.3 mols) of 3-amino-4-methyl-furazan were placed in a 500-ml glass reactor. After cooling to 0°–10° C., 100 g (about 0.6 mols) of cyclohexyl chloroformate were supplied with agitation. The mixture was left to react at ambient temperature (about 20° C.) for an hour and then reflux-heated for 2 hours.

After cooling to ambient temperature, 100 ml water were added to the reaction mixture and the ethereal layer was separated and washed twice with 100 ml water. The ethereal phase was then dried over enhydrous $Na_2SO_4$, the ether was evaporated and the solid residue was purified by crystallization from cyclohexane.

The substance thus obtained was the cyclohexyl ester of 4-methyl-3-furazan-carbamic acid, at 80% of the theoretical yield, in the form of a white crystalline product melting at 114°–115° C.

Elementary analysis: Calculated: C 53.32%; H 6.71%; N 18.65%. Found: C 53.40%; H 6.70%; N 18.10%.

The identity of the product was confirmed by NMR spectroscopy.

EXAMPLES 2–13

A similar method to example 1 was used to prepare compounds corresponding to the preceding general formula (I) in which:

EXAMPLE 2

$R = -CH_3$ $R_1 = -C_2H_5$

The characteristics of this compound may be found in: Farmaco, Ed. Sci., 26 (1971) page 245.

EXAMPLE 3

$R = -CH_3$ $R_1 = -CH_3$

The melting point of this compound is 70°–71° C. (crystallization from benzene and petroleum ether).

EXAMPLE 4

$R = -CH_3$ $R_1 = -(i-C_3H_7)$

The characteristics of this compound may be found in: Farmaco, Ed. Sci., 26 (1971) page 245.

EXAMPLE 5

$R = -CH_3$ $R_1 = -C_6H_5$

Melting point 91°–92° C. (crystallization from cyclohexane).

Elementary analysis: Calculated: C 54.97%; H 4.13%; N 19.17%. Found: C 55.30%; H 4.20%; N. 19.40%.

EXAMPLE 6

$R = -CH_3$ $R_1 = -(i-C_4H_9)$

The characteristics of this compound may be found in: Farmaco Ed. Sci., 26 (1971) page 245.

EXAMPLE 7

$R = -CH_3$ $R_1 = -C_6H_{10}C(CH_3)_3$

Melting point 138°–139° C. (crystallization from cyclohexane).

Elementary analysis: Calculated: C 59.76%; H 8.24%; N 14.93%. Found: C 59.60%; H 8.10%; N 14.65%.

EXAMPLE 8

$R = -CH_3$ $R_1 = -(n-C_4H_9)$

Melting point 52°–53° C. (crystallization from petroleum ether)

Elementary analysis: Calculated: C 48.23%; H 6.57%; N 21.09%. Found: C 48.00%; H 6.50%; N 20.90%.

EXAMPLE 9

$R = -CH_3$ $R_1 = -(2\text{-ethyl hexyl})$

This product is in the form of oil at ambient temperature.

EXAMPLE 10

R=—CH$_3$

R$_1$=—CH$_2$—CH$_6$H$_5$

Melting point 114°–115° C. (crystallization from cyclohexane)

EXAMPLE 11

R=—C$_6$H$_5$

R$_1$=—C$_2$H$_5$

Melting point 68°–69° C. (crystallization from petroleum ether)

EXAMPLE 12

R=—CH$_3$

R$_1$=—(sec. butyl)

Melting point 71°–72° C. (crystallization for petroleum ether)

Elementary analysis: Calculated: C 48.24%; H 6.58%; N 21.09%. Found: C 48.90%; H 6.75%; N 21.50%.

EXAMPLE 13

R=—CH$_3$

R$_1$=—(allyl)

Melting point 53°–55° C. (crystallization from cyclohexane).

The identity of the products obtained in Examples 2 to 13 was also confirmed by NMR spectroscopy.

EVALUATION OF HERBICIDAL ACTIVITY

All the plants were grown in sterile ground and fertilized in a greenhouse at a controlled temperature (20°±5° C.) at 60±10% relative humidity. All species were then cultivated in plastic pots measuring 22×15×6 cm. The compounds described in the preceding examples were formulated in the form of sprayable powders of water/acetone solution or suspension containing 10% of active principle.

PRE-EMERGENCE TEST

Pots containing a suitable number of seeds of each species were treated 24 hours after sowing.

Treatment, both before and after emergence, was given at the dose of 2 and 5 kg/ha, using an Oxford precision pump at a pressure of 5 psi. (0.35 Bars).

Results were obtained after 10 days of treatment in the post-emergence test and after 15–20 days of treatment in the pre-emergence test.

The effect of the active principle was evaluated on a scale from 0 to 4 in which:

0=no damage
1=25% damage
2=50% damage
3=75% damage
4=100% damage

In the following Tables:

Table 1 gives the pre-emergence results for 5 kg/ha of active principle;

Table 2 gives the post-emergence results for 5 kg/ha of active principle;

Table 3 gives the post-emergence results for 2 kg/ha of active principle, thus indicating the selectivity of the active principles described in the preceding experimental examples, with regard to the more important crops and their herbicidal activity with regard to some species of plants.

TABLE 2

|  | Active Principle | | | |
|---|---|---|---|---|
|  | Ex. 1 | Ex. 6 | Ex. 12 | Ex. 13 |
| Beta vulgaris | 4 | 2 | 2 | 2 |
| Pisum sativum | 4 | 2 | 0 | 1 |
| Solanum licopersicum | 4 | 2 | 4 | 4 |
| Cichorium inthibus | 4 | 2 | 4 | 4 |
| Linum usatissimum | 4 | 3 | 3 | 2 |
| Zea mays | 2 | 1 | 1 | 1 |
| Lolium italicum | 2 | 0 | 0 | 0 |
| Avena sativa | 2 | 1 | 0 | 0 |

TABLE 3

|  | Active principle | | | | | | | | | | | | |
|---|---|---|---|---|---|---|---|---|---|---|---|---|---|
|  | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 |
| Beta vulgaris | 4 | 4 | 0 | 4 | 1 | 4 | 1 | 2 | 0 | 3 | 0 | 4 | 3 |
| Pisum sativum | 4 | 3 | 0 | 4 | 2 | 4 | 2 | 3 | 0 | 4 | 0 | 4 | 2 |
| Solanum licopersicum | 4 | 4 | 2 | 4 | 1 | 4 | 2 | 3 | 0 | 3 | 2 | 4 | 4 |
| Cichorium inthibus | 4 | 4 | 3 | 4 | 1 | 4 | 1 | 4 | 0 | 3 | 3 | 4 | 3 |
| Linum usatissimum | 4 | 4 | 3 | 4 | 2 | 4 | 1 | 4 | 1 | 3 | 1 | 4 | 4 |
| Zea mays | 4 | 0 | 1 | 4 | 0 | 3 | 0 | 1 | 0 | 2 | 0 | 2 | 1 |
| Lolium italicum | 4 | 0 | 1 | 3 | 0 | 3 | 0 | 1 | 0 | 2 | 0 | 2 | 1 |
| Avena sativa | 4 | 0 | 0 | 4 | 0 | 2 | 0 | 0 | 0 | 1 | 0 | 2 | 1 |

TABLE 4

|  | Active principle | | |
|---|---|---|---|
|  | Ex. 1 | Ex. 4 | Ex. 6 |
| Soya | 3 | 4 | 2 |
| Rice | 0 | 1 | 1 |
| Maize | 0 | 1 | 0 |
| Oats | 2 | 1 | 1 |
| Wheat | 0 | 2 | 0 |
| Beet | 4 | 4 | 4 |

TABLE 4-continued

| | Active principle | | |
|---|---|---|---|
| | Ex. 1 | Ex. 4 | Ex. 6 |
| Camomile | 4 | 4 | 4 |
| Veronica | 4 | 4 | 3 |
| Polygonum | 4 | 4 | 3 |
| Digitaria | 3 | 1 | 1 |
| Setaria | 3 | 1 | 1 |
| Alopercurus | 4 | 2 | 1 |

We claim:

1. A method of controlling the growth of weeds, before or after the emergence of a crop, characterised in that the infested land is treated with an effective quantity of at least one herbicidal compound chosen from those defined by the following general formula:

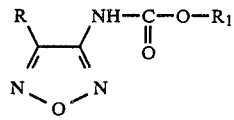

where
R is a straight-chain or branched alkyl group with 1 to 6 carbon atoms or the phenyl group,
$R_1$ is a straight-chain or banched alkyl group with 1 to 10 carbon atoms (substituted if required by halide or phenyl group), an alkenyl group, an alkynyl group, a cycloalkyl group, or the phenyl group.

2. A method according to claim 1, characterised in that the land is treated with from 0.1 to 5 kg/ha of the herbicidal compound.

3. A method according to claim 1, characterised in that the herbicidal compound is applied in the post-emergence period.

* * * * *